(12) United States Patent
Billig et al.

(10) Patent No.: US 7,696,368 B2
(45) Date of Patent: Apr. 13, 2010

(54) START-UP OF HIGH SELECTIVITY CATALYSTS IN OLEFIN OXIDE PLANTS

(75) Inventors: Barry Jay Billig, Irvington, NY (US); James Mann, Little Ferry, NJ (US); Norma Beatriz Castagnola, East Windsor, NJ (US); Christian Gueckel, Munich (DE); Andrzej Rokicki, Mountain Lakes, NJ (US)

(73) Assignee: SD Lizenzverwertungsgesellschaft mbH & Co. KG, Munich (DE)

( * ) Notice: Subject to any disclaimer, the term of this patent is extended or adjusted under 35 U.S.C. 154(b) by 2 days.

(21) Appl. No.: 12/116,653

(22) Filed: May 7, 2008

(65) Prior Publication Data

US 2008/0306291 A1 Dec. 11, 2008

Related U.S. Application Data

(60) Provisional application No. 60/917,621, filed on May 11, 2007.

(51) Int. Cl.
*C07D 301/10* (2006.01)
(52) U.S. Cl. ........................... 549/534; 549/536
(58) Field of Classification Search ................. 549/534, 549/536; 502/217, 347
See application file for complete search history.

(56) References Cited

U.S. PATENT DOCUMENTS

| 4,010,155 | A | 3/1977 | Inouye et al. |
|---|---|---|---|
| 4,012,425 | A | 3/1977 | Nielsen et al. |
| 4,039,561 | A | 8/1977 | Mitsuhata et al. |
| 4,066,575 | A | 1/1978 | Winnick |
| 4,123,385 | A | 10/1978 | Rebsdat et al. |
| 4,350,616 | A | 9/1982 | Boussert |
| 4,761,394 | A | 8/1988 | Lauritzen |
| 4,766,105 | A | 8/1988 | Lauritzen |
| 4,808,738 | A | 2/1989 | Lauritzen |
| 4,820,675 | A | 4/1989 | Lauritzen |
| 4,833,261 | A | 5/1989 | Lauritzen |
| 4,874,879 | A | 10/1989 | Lauritzen et al. |
| 5,155,242 | A | 10/1992 | Shankar et al. |
| 7,102,022 | B2 | 9/2006 | Evans et al. |
| 2004/0049061 | A1 | 3/2004 | Lockemeyer et al. |
| 2004/0059139 | A1 | 3/2004 | Cooker et al. |
| 2004/0110971 | A1 | 6/2004 | Evans et al. |

FOREIGN PATENT DOCUMENTS

EP 0 352 850 1/1990

OTHER PUBLICATIONS

Brunauer, Stephen, et al., "Adsorption of Gases in Multimolecular Layers," J. Am. Chem. Soc. 60 (1938) pp. 309-316.

*Primary Examiner*—Bernard Dentz
*Assistant Examiner*—David E Gallis
(74) *Attorney, Agent, or Firm*—Scully, Scott, Murphy & Presser, P.C.

(57) ABSTRACT

A method to achieve a controlled start-up temperature of an expoxidation process which exceeds the maximum achievable temperature of the epoxidation reactor relative to using an external heat source. The method of the present invention employs an oxidation reaction within the reactor to bring the temperature of the reactor to a temperature that is suitable for conditioning a high selectivity catalyst. The method of the present invention includes first bringing a reactor including a high selectivity catalyst to a first temperature using the external heat source to the reactor, while staying within the reactor design limitations and maintaining a gas flow to the reactor that is within 25 to 100% of the design rates. Once the reactor has achieved the first temperature, at least an olefin, e.g., ethylene, and then oxygen are introduced to the reactor feed gas. The olefin and oxygen concentrations are adjusted to have a heat of reaction that will allow raising the reactor gas flow to 100% of design and then have sufficient heat of reaction to raise the reactor temperature to a second temperature which is greater than the first temperature and greater than the temperature of the reactor achievable by the external heat source.

17 Claims, No Drawings

START-UP OF HIGH SELECTIVITY CATALYSTS IN OLEFIN OXIDE PLANTS

RELATED APPLICATIONS

This application claims benefit of U.S. Provisional Application Ser. No. 60/917,621, filed May 11, 2007.

FIELD OF THE INVENTION

The present invention relates to a start-up process for the epoxidation of an olefin, especially ethylene, to an olefin oxide, especially ethylene oxide, in which a high selectivity silver-based catalyst is employed. The present invention also relates to a process for the epoxidation of an olefin to an olefin oxide utilizing the inventive start-up procedure.

BACKGROUND OF THE INVENTION

The catalytic epoxidation of an olefin in the presence of a silver-based catalyst producing an olefin oxide is well known in the art. Conventional silver-based catalysts have provided an olefin oxide with notoriously low selectivity. As such, when using conventional silver-based catalysts in the epoxidation of an olefin, the selectivity towards the olefin oxide, expressed as a fraction of the olefin converted, does not reach the theoretically maximal selectivity based on the stoichiometry of the reaction.

To a large extent, the selectivity determines the economical attractiveness of an epoxidation process. For example, a one percent improvement in the selectivity of the epoxidation process can reduce the yearly operating costs of a large-scale olefin oxide plant substantially.

As is known to those skilled in the art, an olefin oxide produced by epoxidation using a silver-based catalyst may be reacted with water, an alcohol or an amine to form a 1,2-diol, a 1,2-diol ether or an alkanolamine. For example, ethylene oxide may be reacted with water to form ethylene glycol which product can be used as a component of an antifreeze composition, a solvent or a base material in the production of polyethylene terephthalates. Any improvement in the selectivity of the epoxidation process can also reduce the yearly operating costs in the overall process for the production of these products.

Highly selective silver-based epoxidation catalysts have been developed which extend the selectivity to a value that is closer to the stoichiometric limit mentioned above. Such highly selective catalysts comprise a porous refractory support such as alpha alumina, which has on its surface a catalytic amount of silver and at least one promoter that improves the catalyst performance in the epoxidation process.

The use of alkali metals and transition metals as promoters for silver catalysts is well known for the production of ethylene oxide by the partial oxidation of ethylene in the vapor phase; see, for example, U.S. Pat. Nos. 4,010,155, 4,012,425, 4,123,385, 4,066,575, 4,039,561 and 4,350,616. Highly selective catalysts which contain, in addition to silver, selectivity-enhancing promoters such as rhenium, molybdenum, tungsten or nitrate- or nitrite-forming compounds, are discussed in U.S. Pat. Nos. 4,761,394 and 4,766,105. The catalyst may comprise further elements like alkali metals as described in U.S. Pat. Nos. 3,962,136 and 4,010,115.

Over the last two decades, rhenium was described as being effective in improving the selectivity of alkaline metal promoted silver-based catalyst supported by a refractory porous support; see, for example, U.S. Pat. Nos. 4,761,394 and 4,833,261. Further improvement of silver-based catalysts promoted with alkaline metals and rhenium was achieved by the use of sulfur, Mo, W, Cr as is disclosed in U.S. Pat. Nos. 4,766,105, 4,820,675 and 4,808,738.

In using highly selective silver-based epoxidation catalysts as described, a reaction modifier, for example, an organic halide, may be added to the feed for further increasing the selectivity of the process. The use of reaction modifiers is disclosed, for example, in EP-A-352850, U.S. Pat. Nos. 4,761,394 and 4,766,105.

Despite all the advances made in developing high selectivity catalysts (HSCs), these catalysts, like their conventional counterparts, still need to be conditioned during an initial operation phase of the epoxidation process. The conditioning of HSCs is required in order to ensure that the optimal reactivity of the catalyst as well as high selectivity are achieved. The conditioning process typically occurs during the start-up of the epoxidation reaction, i.e., prior to obtaining a sufficient amount of olefin oxide product.

The start-up process and hence preconditioning of epoxidation catalysts has also been described in the prior art. For example, U.S. Pat. No. 5,155,242 relates to the start-up of an epoxidation process wherein a non-HSC catalyst is subjected to a pre-soak period in the presence of the organic halide at a temperature less than the operating temperature of the reactor. U.S. Pat. No. 4,874,879 relates to the start-up of an epoxidation process wherein a HSC is subjected to a pre-soak period in the presence of the organic halide at a temperature less than the operating temperature of the reactor.

In addition to these disclosures, U.S. Pat. No. 7,102,022 discloses another start-up process for using a HSC. In accordance with this disclosure, the process includes the steps of contacting a catalyst bed comprising a silver-based highly selective epoxidation catalyst, or a precursor of the catalyst comprising the silver in cationic form, with a feed comprising oxygen at a temperature of the catalyst bed above 260° C. for a period of at most 150 hours, and subsequently decreasing the temperature of the catalyst bed to a value of at most 260° C. Another such start-up process is disclosed in U.S. Patent Application Publication No. 2004/0049061 A1 in which a supported highly selective epoxidation catalyst comprising silver in a quantity of at most 0.17 g per m² surface area of the support is used. In accordance with this publication, the method includes contacting the catalyst, or a precursor of the catalyst comprising the silver in cationic form, with a feed comprising oxygen at a catalyst temperature above 250° C. for a duration of up to 150 hours, and subsequently decreasing the catalyst temperature to a value of at most 250° C.

None of the above disclosures provides an effective means for controlling and maintaining the start-up temperature of an epoxidation process as well as controlling the oxygen outlet concentration. As such, there is a need for providing a method in which a HSC can be conditioned at a controlled start-up temperature which exceeds the maximum achievable utilizing an external heating source, such as steam, available to the epoxidation reactor.

SUMMARY OF THE INVENTION

The present invention provides a method to achieve a controlled start-up temperature of an epoxidation process which exceeds the maximum achievable reactor temperature by using an external heat source. Typically, the present invention reaches a start-up temperature that is within a range from about 240° to about 290° C. The method of the present invention employs an internal oxidation reaction within the reactor to bring the temperature of the reactor, and hence the catalyst bed, to a temperature that is suitable for conditioning a high selectivity catalyst.

The method of the present invention includes first bringing a reactor including a high selectivity catalyst and a gas which is passed over the catalyst to a first temperature using an external heat source, for example steam, while staying within the reactor design limitations and maintaining a gas flow to the reactor that is within 25 to 100% of the design rates. For a boiling water type reactor, 100% of design gas rates are typically available and are preferred in some embodiments of the present invention. For a hot oil type reactor, the heat transfer area for heating is generally limited therefore lower gas rates may be required.

Throughout the application, the term "reactor design limitations" is used to denote the maximum temperature (or pressure) that a shell side of an EO reactor can run at. This is referred to as the maximum operating temperature (or pressure). Note that temperature and pressure are interchangeable as temperature and pressure can be looked up on a steam table therefore given one, the other is also defined. The maximum operation temperature of a reactor may vary and is well within the knowledge of one skilled in the art. Typically, the maximum operation temperature for a conventional EO catalyst is up to 290° C., preferably up to 280° C.

The term "design rate" is used throughout the application to denote a capacity that a reactor was designed for, which can be a contractual rate or a rate the sets the volume of catalyst that is used. Normally, when referring to a reactor the design rate is the production rate (or MT/YR of ethylene oxide that the reactor was designed for). It is observed that the design rate is not a limitation on the reactor as a reactor may operate at 150% of design. Moreover, it is observe that the design rate may vary and is well within the knowledge of one skilled in the art as well.

Once the reactor has achieved the first temperature (which is typically from about 220° to about 250° C.), at least an olefin, e.g., ethylene, and then oxygen are introduced to the reactor feed gas. During this introduction process, the olefin concentration within the reactor builds up to a value that is typically within a range from about 5 to about 15%. A moderator can also be introduced prior to the introduction of oxygen to build up the moderating agent level in the feed gas to a value that is typically from about 1 to about 10 ppm. Oxygen is then introduced to the feed gas. It is noted that the moderating agent level may build over time as initially the HSC catalyst that is present in the reactor may absorb the moderating agent in the feed gas. Oxygen is typically brought to a concentration that is within a range from about 0.5% to about the flammable limit at the reactor inlet and is subsequently adjusted to maintain an oxygen concentration at the reactor outlet of greater than 0.5%.

During the aforementioned introduction step, the olefin and oxygen concentrations are adjusted to generate enough heat of reaction that will allow raising the reactor gas flow to 100% of design and then have still sufficient heat of reaction to raise the reactor temperature to a second temperature which is greater than the first temperature and greater than the reactor temperature which can be achieved by the external heat source. Typically, the second temperature is within a range from about 240° to about 290° C. This second temperature is maintained within the reactor for a time period from about 0.15 to about 200 hours.

This second temperature within the reactor, which is achieved by the heat of reaction, is controlled by adjusting composition of the feed gas. The composition of the feed gas has to be adjusted to counteract the loss of catalyst activity which occurs during the conditioning procedure. Also, temperature control is maintained in the present invention by a cooling medium of the reactor.

Additionally, efficient conditioning of the catalyst requires an exact monitoring and controlling of the concentration level of oxygen at the reactor outlet. When the oxygen level at the reactor outlet is not at the desirable level, typically greater than 0.5%, the feed gas composition at the reactor inlet can be adjusted to achieve the aforementioned oxygen outlet concentration, i.e., the olefin, the oxygen, carbon dioxide and/or the moderator can be adjusted.

Other ways of controlling the oxygen outlet concentration can be the selected from following list:
1. Adjusting the reactor temperature
2. Adjusting the reactor pressure
3. Adjusting the gas flow The preferred embodiment of the invention is the controlling of the oxygen concentration at the reactor outlet at a value of greater than 0.5% by adjusting the inlet concentrations of ethylene, oxygen and/or carbon dioxide. The most preferred embodiment of controlling the oxygen concentration at the reactor outlet is by adjusting the ethylene and/or oxygen concentration at the reactor inlet.

In some embodiments, a low oxygen concentration in the feed gas can be employed by utilizing an oxygen mixing station. The oxygen mixing station aids in controlling the amount of oxygen that is introduced into the feed gas which, in turn, helps to control the concentration of oxygen that exits the system from the reactor outlet.

The inventive method allows for increasing the reactor temperature above a level attainable by steam or limited by the design pressure of the reactor.

With the reaction, the temperature of the HSC in the reactor tube is as high as 10° C. above the reactor heat transfer medium temperature. The presence of the heat of reaction described above allows a lower reactor temperature than would be required if no reaction was present. This extends the catalyst heat-treating stage to take place at lower reactor coolant temperatures, thereby achieving higher catalyst's temperature beyond the limits of both the heating system or the design condition of the reactor heater.

DETAILED DESCRIPTION OF THE INVENTION

As stated above, the invention provides a method to achieve a controlled start-up temperature of an epoxidation process which exceeds the maximum temperature of the epoxidation reactor achievable by heating the reactor with an external heat source, for example, with steam. The method of the present invention employs oxidation reactions within the reactor to bring the temperature of the reactor to a temperature that is suitable for conditioning a high selectivity catalyst.

The olefin used in the epoxidation process may be any olefin, such as an aromatic olefin, for example, styrene or a di-olefin, whether conjugated or not, for example, 1,9-decadiene or 1,3-butadiene. Typically, the olefin is a monoolefin, for example, 2-butene or isobutene. Preferably, the olefin is a mono-alpha-olefin such as 1-butene or propylene. The most preferred olefin is ethylene.

The method of the present invention includes first bringing a reactor including a high selectivity catalyst and an initial feed gas to a first temperature using an external heat source, for example steam, while staying within the reactor design limitations and maintaining a gas flow to the reactor that is within 25 to 100% of the design rates. Once the reactor has achieved the first temperature, at least an olefin, e.g., ethylene, and then oxygen are introduced to the reactor feed gas.

During this introduction process, the olefin concentration within the reactor builds up to a value that is typically within a range from about 5 to about 15%. A moderator can also be introduced prior to the introduction of oxygen to build up the moderating agent level in the feed gas to a value that is typically from about 1 to about 10 ppm. Oxygen is then introduced to the feed gas. It is noted that the moderating agent level may build over time as initially the HSC catalyst that is present in the reactor may absorb the moderating agent in the feed gas. Oxygen is typically brought to a concentration that is within a range from about 1 to about 10% at the reactor inlet and is adjusted along with at least the olefin concentration to maintain an oxygen concentration at the reactor outlet of greater than 0.5%.

During the aforementioned introduction step, the olefin and oxygen concentrations are adjusted to generate enough heat of reaction that will allow raising the reactor gas flow to 100% of design and then have still sufficient heat of reaction to raise the reactor temperature to a second temperature which is greater than the first temperature and greater than the reactor temperature which can be achieved by the external heat source. Typically, the second temperature is within a range from about 240° to about 290° C. This second temperature is maintained within the reactor for a time period from about 0.15 to about 200 hours.

The various elements of the present invention are now described in greater detail.

The high selectivity catalyst employed in the present invention is any silver-based support catalyst which achieves a selectivity that is greater than 85%. The support employed in this invention may be selected from a large number of solid, refractory supports that may be porous. The support may comprise materials such as alpha-alumina, charcoal, pumice, magnesia, zirconia, titania, kieselguhr, fuller's earth, silicon carbide, silica, silicon carbide, clays, artificial zeolites, natural zeolites, silicon dioxide and/or titanium dioxide, ceramics and combination thereof. A preferred support is comprised of alpha-alumina having a very high purity; i.e., at least 95 wt. % pure, or more preferably, at least 98 wt. % alpha-alumina. The remaining components may include inorganic oxides other than alpha-alumina, such as silica, alkali metal oxides (e.g., sodium oxide) and trace amounts of other metal-containing or non-metal-containing additives or impurities.

The support is preferably porous and has a B.E.T. surface area of at most 20 $m^2/g$, preferably from 0.1 to 10 $m^2/g$, and more preferably from 1 to 5 $m^2/g$. As used herein, the B.E.T. surface area is deemed to have been measured by the method as described in Brunauer, Emmet and Teller in J. Am. Chem. Soc. 60 (1938) 309-316. The support may have a monomodal pore size distribution or a multi-modal pore size distribution.

Regardless of the character of the support used, it is usually shaped into particles, chunks, pieces, pellets, rings, spheres, wagon wheels, cross-partitioned hollow cylinders, and the like, of a size suitable for employment in fixed-bed epoxidation reactors. Desirably, the support particles may have equivalent diameters in the range of from about 3 mm to about 12 mm and preferably in the range of from about 5 mm to about 10 mm, which are usually compatible with the internal diameter of the tubular reactors in which the catalyst is placed. Equivalent diameter is the diameter of a sphere having the same external surface (i.e., neglecting surface within the pores of the particle) to volume ratio as the support particles being employed.

In order to produce a catalyst for the oxidation of ethylene to ethylene oxide, a support having the above characteristics is then provided with a catalytically effective amount of silver on its surface. The catalyst is prepared by impregnating the support with a silver compound, complex or salt dissolved in a suitable solvent sufficient to cause deposition of a silver-precursor compound onto the support. Preferably, an aqueous silver solution is used. After impregnation, the excess solution is removed from the impregnated support, and the impregnated support is heated to evaporate the solvent and to deposit the silver or silver compound on the support as is known in the art.

Preferred catalysts prepared in accordance with this invention contain up to about 45% by weight of silver, expressed as metal, based on the total weight of the catalyst including the support. The silver is deposited upon the surface and throughout the pores of a porous refractory support. Silver contents, expressed as metal, of from about 1% to about 40% based on the total weight of the catalyst are preferred, while silver contents of from about 8% to about 35% are more preferred. The amount of silver deposited on the support or present on the support is that amount which is a catalytically effective amount of silver, i.e., an amount which economically catalyzes the reaction of ethylene and oxygen to produce ethylene oxide. As used herein, the term "catalytically effective amount of silver" refers to an amount of silver that provides a measurable conversion of ethylene and oxygen to ethylene oxide. Useful silver containing compounds which are silver precursors non-exclusively include silver oxalate, silver nitrate, silver oxide, silver carbonate, a silver carboxylate, silver citrate, silver phthalate, silver lactate, silver propionate, silver butyrate and higher fatty acid salts and combinations thereof.

Also deposited on the support, either prior to, coincidentally with, or subsequent to the deposition of the silver is a promoting amount of a rhenium component, which may be a rhenium-containing compound or a rhenium-containing complex. The rhenium promoter may be present in an amount of from about 0.001 wt. % to about 1 wt. %, preferably from about 0.005 wt. % to about 0.5 wt. %, and more preferably from about 0.01 wt. % to about 0.1 wt. % based on the weight of the total catalyst including the support, expressed as the rhenium metal.

Also deposited on the support either prior to, coincidentally with, or subsequent to the deposition of the silver and rhenium are promoting amounts of an alkali metal or mixtures of two or more alkali metals, as well as optional promoting amounts of a Group IIA alkaline earth metal component or mixtures of two or more Group IIA alkaline earth metal components, and/or a transition metal component or mixtures of two or more transition metal components, all of which may be in the form of metal ions, metal compounds, metal complexes and/or metal salts dissolved in an appropriate solvent. The support may be impregnated at the same time or in separate steps with the various catalyst promoters. The particular combination of silver, support, alkali metal promoters, rhenium component, and optional additional promoters of the instant invention will provide an improvement in one or more catalytic properties over the same combination of silver and support and none, or only one of the promoters.

As used herein the term "promoting amount" of a certain component of the catalyst refers to an amount of that component that works effectively to improve the catalytic performance of the catalyst when compared to a catalyst that does not contain that component. The exact concentrations employed, of course, will depend on, among other factors, the desired silver content, the nature of the support, the viscosity of the liquid, and solubility of the particular compound used to deliver the promoter into the impregnating solution. Examples of catalytic properties include, inter alia, operability (resistance to runaway), selectivity, activity, conversion, stability and yield. It is understood by one skilled in the art that one or more of the individual catalytic properties may be enhanced by the "promoting amount" while other catalytic properties may or may not be enhanced or may even be diminished. It is further understood that different catalytic properties may be enhanced at different operating conditions. For example, a catalyst having enhanced selectivity at one set of operating conditions may be operated at a different set of conditions wherein the improvement shows up in the activity rather than the selectivity. In the epoxidation process, it may be desirable to intentionally change the operating conditions to take advantage of certain catalytic properties even at the expense of other catalytic properties. The preferred operating conditions will depend upon, among other factors, feedstock costs, energy costs, by-product removal costs and the like.

Suitable alkali metal promoters may be selected from lithium, sodium, potassium, rubidium, cesium or combinations thereof, with cesium being preferred, and combinations of cesium with other alkali metals, such as lithium, being especially preferred. The amount of alkali metal deposited or present on the support is to be a promoting amount. Preferably, the amount will range from about 10 ppm to about 3000 ppm, more preferably from about 15 ppm to about 2000 ppm, and even more preferably from about 20 ppm to about 1500 ppm, and as especially preferred from about 50 ppm to about 1000 ppm by weight of the total catalyst, measured as the metal.

Suitable alkaline earth metal promoters comprise elements from Group IIA of the Periodic Table of the Elements, which may be beryllium, magnesium, calcium, strontium, and barium or combinations thereof. Suitable transition metal promoters may comprise elements from Groups IVA, VA, VIA, VIIA and VIIIA of the Periodic Table of the Elements, and combinations thereof. Most preferably the transition metal comprises an element selected from Groups IVA, VA or VIA of the Periodic Table of the Elements. Preferred transition metals that can be present include molybdenum, tungsten, chromium, titanium, hafnium, zirconium, vanadium, tantalum, niobium, or combinations thereof.

The amount of alkaline earth metal promoter(s) and/or transition metal promoter(s) deposited on the support is a promoting amount. The transition metal promoter may typically be present in an amount of from about 0.1 micromoles per gram to about 10 micromoles per gram, preferably from about 0.2 micromoles per gram to about 5 micromoles per gram, and more preferably from about 0.5 micromoles per gram to about 4 micromoles per gram of total catalyst, expressed as the metal. The catalyst may further comprise a promoting amount of one or more sulfur compounds, one or more phosphorus compounds, one or more boron compounds, one or more halogen-containing compounds, or combinations thereof. In one embodiment, the catalyst includes from about 5 to about 200 ppm, preferably from about 10 to about 100 ppm sulfur.

The silver solution used to impregnate the support may also comprise an optional solvent or a complexing/solubilizing agent such as are known in the art. A wide variety of solvents or complexing/solubilizing agents may be employed to solubilize silver to the desired concentration in the impregnating medium. Useful complexing/solubilizing agents include amines, ammonia, oxalic acid, lactic acid and combinations thereof. Amines include an alkylene diamine having from 1 to 5 carbon atoms. In one preferred embodiment, the solution comprises an aqueous solution of silver oxalate and ethylene diamine. The complexing/solubilizing agent may be present in the impregnating solution in an amount of from about 0.1 to about 5.0 moles per mole of silver, preferably from about 0.2 to about 4.0 moles, and more preferably from about 0.3 to about 3.0 moles for each mole of silver.

When a solvent is used, it may be an organic solvent or water, and may be polar or substantially or totally non-polar. In general, the solvent should have sufficient solvating power to solubilize the solution components. At the same time, it is preferred that the solvent be chosen to avoid having an undue influence on or interaction with the solvated promoters. Examples of organic solvents include, but are not limited to, alcohols, in particular alkanols; glycols, in particular alkyl glycols; ketones; aldehydes; amines; tetrahydrofuran; nitrobenzene; nitrotoluene; glymes, in particular glyme, diglyme and tetraglyme; and the like. Organic-based solvents which have 1 to about 8 carbon atoms per molecule are preferred. Mixtures of several organic solvents or mixtures of organic solvent(s) with water may be used, provided that such mixed solvents function as desired herein.

The concentration of silver in the impregnating solution is typically in the range of from about 0.1% by weight up to the maximum solubility afforded by the particular solvent/solubilizing agent combination employed. It is generally very suitable to employ solutions containing from 0.5% to about 45% by weight of silver, with concentrations of from 5 to 35% by weight of silver being preferred.

Impregnation of the selected support is achieved using any of the conventional methods; for example, excess solution impregnation, incipient wetness impregnation, spray coating, etc. Typically, the support material is placed in contact with the silver-containing solution until a sufficient amount of the solution is absorbed by the support. Preferably the quantity of the silver-containing solution used to impregnate the porous support is no more than is necessary to fill the pores of the support. A single impregnation or a series of impregnations, with or without intermediate drying, may be used, depending, in part, on the concentration of the silver component in the solution. Impregnation procedures are described in U.S. Pat. Nos. 4,761,394, 4,766,105, 4,908,343, 5,057,481, 5,187,140, 5,102,848, 5,011,807, 5,099,041 and 5,407,888. Known prior procedures of pre-deposition, co-deposition and post-deposition of various the promoters can be employed.

After impregnation of the support with the silver-containing compound, i.e. a silver precursor, rhenium component, alkali metal component, and the optional other promoters, the impregnated support is calcined for a time sufficient to convert the silver containing compound to an active silver species and to remove the volatile components from the impregnated support to result in a catalyst precursor. The calcination may be accomplished by heating the impregnated support, preferably at a gradual rate, to a temperature in the range of from about 200° to about 600° C., preferably from about 200° to about 500° C., and more preferably from about 200 to about 450° C., at a pressure in the range of from 0.5 to 35 bar. In general, the higher the temperature, the shorter the required heating period. A wide range of heating periods have been suggested in the art; e.g., U.S. Pat. No. 3,563,914 suggests heating for less than 300 seconds, and U.S. Pat. No. 3,702,259 discloses heating from 2 to 8 hours at a temperature of from 100° to 375° C., usually for duration of from about 0.5 to about 8 hours. However, it is only important that the heating time be correlated with the temperature such that substantially all of the contained silver is converted to the active silver species. Continuous or step-wise heating may be used for this purpose.

During calcination, the impregnated support may be exposed to a gas atmosphere comprising an inert gas or a mixture of an inert gas with from about 10 ppm to 21% by volume of an oxygen-containing oxidizing component. For purposes of this invention, an inert gas is defined as a gas that does not substantially react with the catalyst or catalyst precursor under the conditions chosen for the calcination. Non-limiting examples include nitrogen, argon, krypton, helium, and combinations thereof, with the preferred inert gas being nitrogen. Non-limiting examples of the oxygen-containing oxidizing component include molecular oxygen ($O_2$), $CO_2$, NO, $NO_2$, $N_2O$, $N_2O_3$, $N_2O_4$, or $N_2O_5$, or a substance capable of forming NO, $NO_2$, $N_2O$, $N_2O_3$, $N_2O_4$, or $N_2O_5$ under the calcination conditions, or combinations thereof, and optionally comprising $SO_3$, $SO_2$, trimethyl phosphite or combinations thereof Of these, molecular oxygen is a useful embodiment, and a combination of $O_2$ with NO or $NO_2$ is another useful embodiment. In a useful embodiment, the atmosphere comprises from about 10 ppm to about 1% by volume of an oxygen-containing oxidizing component. In another useful embodiment, the atmosphere comprises from about 50 ppm to about 500 ppm of an oxygen-containing oxidizing component.

After providing the high selectivity catalyst, it is loaded into reactor tubes of an epoxidation reactor utilizing conventional loading methods well known to those skilled in the art. The inventive start-up process is now performed. Prior to performing the inventive start-up procedure, the catalyst may be swept by passing an inert gas such as nitrogen, over the catalyst bed. The inventive start-up procedure begins by first bringing a reactor including a high selectivity catalyst over which a gas, for example nitrogen, is flowing to a first temperature using an available external heat source, for example steam, while staying within the reactor design limitations and maintaining a gas flow to the reactor that is within 25 to 100% of the design rates.

With the aid of the external heat source, the temperature of the reactor is increased to a first temperature that is typically from about 180° C. to about 250° C. Usually the temperature is held for a time period of from about 0.15 hour or more. In one embodiment the holding is conducted for a time period from about 0.5 hour to about 48 hours.

Once the reactor has achieved the first temperature, at least an olefin, e.g., ethylene, and then oxygen are introduced to the reactor feed gas. During this introduction process, the olefin concentration within the reactor builds up to a value that is typically within a range from about 5 to about 15%. A moderator can also be introduced prior to the introduction of oxygen to build up the moderating agent level in the feed gas to a value that is typically from about 1 to about 10 ppm. Oxygen is then introduced to the feed gas. It is noted that the moderating agent level may build over time as initially the HSC catalyst that is present in the reactor may absorb the moderating agent in the feed gas. Oxygen is typically brought to a concentration that is within a range from about 1 to about 10% at the reactor inlet and is adjusted along with at least the olefin concentration to maintain an oxygen concentration at the reactor outlet of greater than 0.5%.

During the aforementioned introduction step, the olefin and oxygen concentrations are adjusted to generate enough heat of reaction that will allow raising the reactor gas flow to 100% of design and then have still sufficient heat of reaction to raise the reactor temperature to a second temperature which is greater than the first temperature and greater than the reactor temperature which can be achieved by the external heat source. Typically, the second temperature is within a range from about 240° to about 290° C. This second temperature is maintained within the reactor for a time period from about 0.15 to about 200 hours.

This second temperature within the reactor which is achieved by the heat of reaction is controlled by adjusting the feed rates of the various gases that are introduced into the feed gas. Also, temperature control is maintained in the present invention by a cooling medium which surrounds the reactor.

Additionally, efficient conditioning of the catalysts requires an exact monitoring and controlling of the concentration level of oxygen at the reactor outlet. When the oxygen level at the reactor outlet is not at the desirable level, typically greater than 0.5%, the feed gas composition at the reactor inlet can be adjusted to achieve the aforementioned oxygen outlet concentration, i.e., the olefin, the oxygen, carbon dioxide and/or the moderator can be adjusted.

Other ways of controlling the oxygen outlet concentration can be the selected from following list:
4. Adjusting the reactor temperature
5. Adjusting the reactor pressure
6. Adjusting the gas flow The preferred embodiment of the invention is the controlling of the oxygen concentration at the reactor outlet at a value of greater than 0.5% by adjusting the inlet concentrations of ethylene, oxygen and/or carbon dioxide. The most preferred embodiment of controlling the oxygen concentration at the reactor outlet is by adjusting the ethylene and/or oxygen concentration at the reactor inlet.

A low and precise oxygen concentration in the gas feed can be employed by utilizing an oxygen mixing station. The oxygen mixing station controls the amount of oxygen that is introduced into the feed gas which helps to control that which exiting the system from the reactor outlet.

The inventive method allows for increasing the reactor temperature above a level attainable by an external heat source or limited by the design pressure of the reactor.

With the reaction, the temperature of the catalyst bed in the reactor tube is as high as 10° C. above the reactor coolant temperature. The presence of the heat of reaction described above allows a lower reactor temperature than would be required if no reaction was present. This extends the catalyst heat treating stage to take place at lower reactor coolant temperatures, thereby achieving the higher catalysts temperature beyond the limits of both the heating system or the design condition of the reactor heater.

The epoxidation process may be carried out by continuously contacting an oxygen-containing gas with an olefin, which is preferably ethylene, in the presence of a HSC catalyst as mentioned above. Oxygen may be supplied to the reaction in substantially pure molecular form or in a mixture such as air. Molecular oxygen employed as a reactant may be obtained from conventional sources. Reactant feed mixtures may contain from about 0.5% to about 45% ethylene and from about 3% to about 15% oxygen, with the balance comprising comparatively inert materials including such substances as carbon dioxide, water, inert gases, other hydrocarbons, and one or more reaction modifiers such as organic halides, inorganic halides, nitrogen oxides, phosphorus compounds, sulfur compounds and mixtures thereof Non-limiting examples of inert gases include nitrogen, argon, helium and mixtures thereof. Non-limiting examples of the other hydrocarbons include methane, ethane, propane and mixtures thereof. Carbon dioxide and water are byproducts of the epoxidation process as well as common contaminants in the feed gases. Both have adverse effects on the catalyst, so the concentrations of these components are usually kept at a minimum. Non-limiting examples of reaction moderators include organic halides such as $C_1$ to $C_8$ halohydrocarbons. Preferably, the reaction moderator is methyl chloride, ethyl chloride, ethylene dichloride, ethylene dibromide, vinyl chloride or mixtures thereof. Most preferred reaction moderators are ethyl chloride and ethylene dichloride. Usually such reaction moderators are employed in an amount of from about 0.5 to 10 ppmv, preferably from 1 to 8 ppmv of the total volume of the feed gas.

A usual method for the ethylene epoxidation process comprises the vapor-phase oxidation of ethylene with molecular oxygen, in the presence of a HSC, in a fixed-bed tubular reactor. Conventional, commercial fixed-bed ethylene-oxide reactors are typically in the form of a plurality of parallel elongated tubes (in a suitable shell) approximately 0.7 to 2.7 inches O.D. and 0.5 to 2.5 inches I.D. and 15-45 feet long filled with catalyst. Typical operating conditions for the ethylene epoxidation process involve temperatures in the range of from about 180° to about 330° C., and preferably, about 200° to about 325° C., and more preferably from about 225° to about 270° C. The operating pressure may vary from about atmospheric pressure to about 30 atmospheres, depending on the mass velocity and productivity desired. Higher pressures may be employed within the scope of the invention. Residence times in commercial-scale reactors are generally on the order of about 0.1-5 seconds.

The resulting ethylene oxide is separated and recovered from the reaction products using conventional methods. For this invention, the ethylene epoxidation process may include a gas recycle wherein substantially all of the reactor effluent is readmitted to the reactor inlet after substantially or partially removing the ethylene oxide product and the byproducts. In the recycle mode, carbon dioxide concentrations in the gas inlet to the reactor may be, for example, from about 0.3 to 6 volume percent.

The inventive method is particularly suitable for oxidation of ethylene with molecular oxygen to ethylene oxide. The conditions for carrying out such an oxidation reaction in the presence of the catalysts of the present invention broadly comprise those described in the prior art. This applies to suitable temperatures, pressures, residence times, diluent materials, moderating agents, and recycle operations, or applying successive conversions in different reactors to increase the yields of ethylene oxide. For purposes of illustration only, the following are conditions that are often used in current commercial ethylene oxide reactor units: a gas hourly space velocity of 1500-10,000 $h^{-1}$, a reactor inlet pressure of 150-400 psig, a coolant temperature of 180-315° C., an oxygen conversion level of 10-60%, and an EO production rate (work rate) of 2-16 lbs. EO/cu.ft. catalyst/hr. The feed composition at the reactor inlet may typically comprises 1-40% ethylene, 3-12% $O_2$, 0.3-40% $CO_2$, 0-3% ethane, 0.3-20 ppmv total concentration of organic chloride moderator(s), and the balance of the feed being comprised of argon, methane, nitrogen or mixtures thereof.

While the present invention has been particularly shown and described with respect to preferred embodiments thereof, it will be understood by those skilled in the art that the foregoing and other changes in forms and details may be made without departing from the spirit and scope of the present invention. It is therefore intended that the present invention not be limited to the exact forms and details described and illustrated, but fall within the scope of the appended claims.

What is claimed is:

1. A method to achieve a controlled start-up temperature of an epoxidation process comprising:
   bringing a reactor including a high selectivity catalyst to a first temperature by an external heat source of the reactor, while staying within reactor design limitations and maintaining a gas flow to the reactor that is within 25 to 100% of design rates; and
   subsequently introducing at least an olefin and then oxygen to the feed gas to cause a heat of reaction within said reactor to raise the first temperature to a second temperature which is greater than the first temperature, and controlling the concentration of oxygen at a reactor outlet to be greater than about 0.5%.

2. The method of claim 1 wherein the second temperature within the reactor is controlled by adjusting the feed rate of at least one of said olefin, oxygen, $CO_2$ and/or moderator.

3. The method of claim 1 wherein said controlling is achieved by changing the flow of one of the olefin, oxygen, carbon dioxide and/or moderator in said gas feed.

4. The method of claim 3 wherein said oxygen flow is adjusted utilizing an oxygen mixing station.

5. The method of claim 1 wherein the second temperature exceeds the maximum reactor coolant temperature.

6. The method of claim 1 wherein said high selectivity catalyst includes silver in an amount up to 45% by weight.

7. The method of claim 6 wherein said silver is supported on a solid refractory support having a surface area of at most 20 $m^2/gm$.

8. The method of claim 7 wherein said solid refractory support is alpha alumina.

9. The method of claim 6 further comprising a promoting amount of rhenium.

10. The method of claim 9 wherein said promoting amount of rhenium is from about 0.01 wt. % to about 1 wt. %.

11. The method of claim 9 further comprising a promoting amount of at least one alkali metal.

12. The method of claim 9 further comprising a combination of lithium and cesium.

13. The method of claim 6 further comprising a promoting amount of at least one transition metal selected from Mo, W, Cr, Ti, Hf, Zr, V, Ta and Nb.

14. The method of claim 1 wherein said high selectivity catalyst is a calcined catalyst.

15. The method of claim 6 further comprising a promoting amount of sulfur.

16. The method of claim 1 wherein said first temperature is from about 180° C. to about 250° C.

17. The method of claim 1 wherein said second temperature is from about 240° C. to about 290° C.

* * * * *